US00PP19265P2

(12) United States Plant Patent
Pieters

(10) Patent No.: US PP19,265 P2
(45) Date of Patent: Sep. 23, 2008

(54) *CHRYSANTHEMUM* PLANT NAMED 'PPP CEDR06'

(50) Latin Name: *Chrysanthemum morifolium*
Varietal Denomination: PPP CEDR06

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 11/823,255

(22) Filed: Jun. 27, 2007

(51) Int. Cl.
*A01H 5/00* (2006.01)

(52) U.S. Cl. ..... Plt./292

(58) Field of Classification Search ..... Plt./292
See application file for complete search history.

(56) References Cited

U.S. PATENT DOCUMENTS

PP13,807 P3 * 5/2003 Pieters ..... Plt./293
PP14,404 P3 * 12/2003 Pieters ..... Plt./287

* cited by examiner

*Primary Examiner*—Wendy C. Haas

(57) ABSTRACT

A new and distinct *Chrysanthemum* plant cultivar is disclosed, characterized by large decorative type inflorescences, consistent flowering response to short days, blooming consistently after 49 days of short day length, pink ray florets, free branching habit, and a consistent natural season flowering habit during the last week of September.

1 Drawing Sheet

Latin name of the genus and species: *Chrysanthemum morifolium.*
Variety denomination: 'PPP CEDR06'.

BACKGROUND OF THE INVENTION

The new cultivar 'PPP CEDR06' is a product of a cross between the male parent 'Remos' (not patented in the United States) and the female parent 'GEDI ONE GAL' (U.S. Plant Pat. No. 13,807). The new cultivar was discovered and selected by Dirk Pieters in September of 2002 in Oostnieuwkerke, Belgium.

Asexual reproduction of the new cultivar 'PPP CEDR06' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP CEDR06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP CEDR06.' These characteristics in combination distinguish 'PPP CEDR06' as a new and distinct *Chrysanthemum* cultivar.

1. Large, pink decorative-type inflorescences;
2. Free branching habit;
3. Consistent natural season flowering habit during the last week in September; and
4. Consistent flowering response to short days, blooming consistently after 49 days of short day length.

Plants of the new cultivar 'PPP CEDR06' are similar to plants of the male parent variety, 'Remos' in most horticultural characteristics, however plants of the new cultivar 'PPP CEDR06' are smaller in both height and plant spread. Also, the new cultivar 'PPP CEDR06' has a smaller inflorescence diameter than the male parent and different color ray florets. Finally, 'PPP CEDR06' blooms two weeks earlier than the male parent 'Remos.'

Plants of the new cultivar 'PPP CEDR06' are similar to plants of the female parent variety, 'GEDI ONE GAL' in most horticultural characteristics; however plants of the new cultivar 'PPP CEDR06' are shorter. Also, the new cultivar 'PPP CEDR06' has a smaller inflorescence diameter and more inflorescences per lateral branch. Additionally, 'PPP CEDR06' has longer inflorescence longevity. Finally, 'PPP CEDR06' has lighter pink-purple ray florets compared to the dark purple ray florets of the female parent.

In comparison to the commercially available variety 'GEDI TWO COP' (U.S. Plant Pat. No. 14,404), 'PPP CEDR06' has a wider plant spread. Also, the new variety 'PPP CEDR06' has longer inflorescence longevity. Additionally, the new variety 'PPP CEDR06' blooms one week later. Finally, the ray florets of the new variety 'PPP CEDR06' are a lighter pink.

BRIEF DESCRIPTION OF THE PHOTOGRAPH

The accompanying photograph illustrates in full color a typical plant of 'PPP CEDR06' grown in a 2 gallon container. One cutting was used in the pot, planted mid May and growth under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP CEDR06' plants grown in Oxnard, Ventura County, Calif., during the months of May through October 2006. The growing temperature ranged from 12° C. to 15° C. at night to 12° C. to 20° C. during the day. Measurements a numerical values represent averages of typical flowering types.

Botanical classification: *Chrysanthemum morifolium* cultivar 'PPP CEDR06'.
Commercial classification: Garden-type *Chrysanthemum.*

PROPAGATION

Time to Rooting: 7 to 14 days at approximately 21° C.
Root Description: Fine, fibrous.

PLANT

Growth Habit: Mounding herbaceous perennial.
Height: Approximately 21 cm.
Plant Spread: Approximately 42 cm.
Growth Rate: Moderate.
Branching Characteristics: Free Branching.
Length of Lateral Branches: Approximately 15 cm.
Number of Leaves per Lateral Branch: Approximately 26.
Age of Plant Described: Approximately 153 days.

FOLIAGE

Leaf:
*Arrangement.*—Alternate single.
*Average length.*—Approximately 5 cm.
*Average width.*—Approximately 2.8 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 0.7 cm.
*Color.*—Young foliage upper side: Near Green 137B. Young foliage under side: Near Green 137C. Mature foliage upper side: Near Yellow-Green 147A. Mature foliage under side: Near Yellow-Green 147B.
*Venation.*—Type: Palmately net. Venation color upper side: Near Yellow-Green 147C. Venation color under side: Near Yellow-Green 147D.

Petiole:
*Average Length.*—Approximately 1.3 cm.
*Color.*—Near Yellow-Green 147D.
*Diameter.*—Approximately 0.2 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last week in September.
*Number of inflorescences per lateral branch.*—Approximately 18.
*Inflorescence diameter.*—Approximately 4.8 cm.
*Inflorescence depth.*—Approximately 1.8 cm.
*Inflorescence longevity on plant.*—Approximately 28 to 32 days.
*Persistence.*—Persistent.

Ray florets:
*Appearance.*—Matte.
*Texture.*—Smooth.
*Average number of ray florets per inflorescence.*—111.
*Shape.*—Oblanceolate.
*Aspect.*—Flat.
*Margin.*—Entire.
*Apex.*—Obtuse.
*Length.*—Approximately 2.6 cm.
*Width.*—Approximately 0.8 cm.
*Color.*—Upper surface at first opening: Near Red-Purple 58A. Upper surface at maturity: Near Red-Purple 65B. Upper surface at fading: Near Red-Purple 65C. Under surface at first opening: Near Red-Purple 58A. Under surface at maturity: Near Red-Purple 70D. Under surface at fading: Near Red-Purple 70D.

Disc florets:
*Appearance.*—Shiny.
*Texture.*—Smooth.
*Average number of florets per disc.*—Approximately 43.
*Shape.*—Cylindric.
*Apex.*—Obtuse.
*Average length.*—Approximately 0.3 cm.
*Average width.*—Approximately 0.1 cm.
*Color.*—At first opening: Near Yellow 13B. At maturity: Near Yellow 13A. At fading: Near Yellow 13A.

Peduncle:
*Length.*—At terminal end (shortest): Approximately 3 cm. At lateral end (longest): Approximately 5 cm.
*Angle to stem.*—Acute.
*Strength.*—Moderate.
*Color.*—Near Green 137A.
*Habit.*—Upright.
*Diameter.*—Approximately 0.2 cm.
*Surface texture.*—Lightly pubescent.

Inflorescence bud:
*Length.*—Approximately 1.2 cm.
*Diameter.*—Approximately 1 cm.
*Form.*—Globular.
*Color.*—Near Red-Purple 58A.

Involucral bracts (phyllaries):
*Appearance.*—Matte.
*Texture.*—Lightly pubescent.
*Number.*—Approximately 28.
*Shape.*—Ovate.
*Margin.*—Entire.
*Apex.*—Entire.
*Length.*—Approximately 0.8 cm.
*Width.*—Approximately 0.3 cm.
*Color.*—Upper side: Near Green 137A. Under side: Near Green 137B.

REPRODUCTIVE ORGANS

Ray florets:
*Number of pistils per floret.*—1.
*Stigma shape.*—2 branched.
*Stigma color.*—Near Yellow 12B.
*Style color.*—Near Green-Yellow 1D.
*Style length.*—Approximately 0.4 cm.
*Stamens.*—Absent.

Disc florets:
*Number of pistils per floret.*—1.
*Stigma shape.*—Cylindric.
*Stigma color.*—Near Yellow 12A.
*Style length.*—Approximately 0.2 cm.

*Style color.*—Near Green-Yellow 1C.
*Number of stamens per floret.*—Approximately 5.
*Anther shape.*—Tubular.
*Anther color.*—Near Yellow 12A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP CEDR06' as herein illustrated and described.

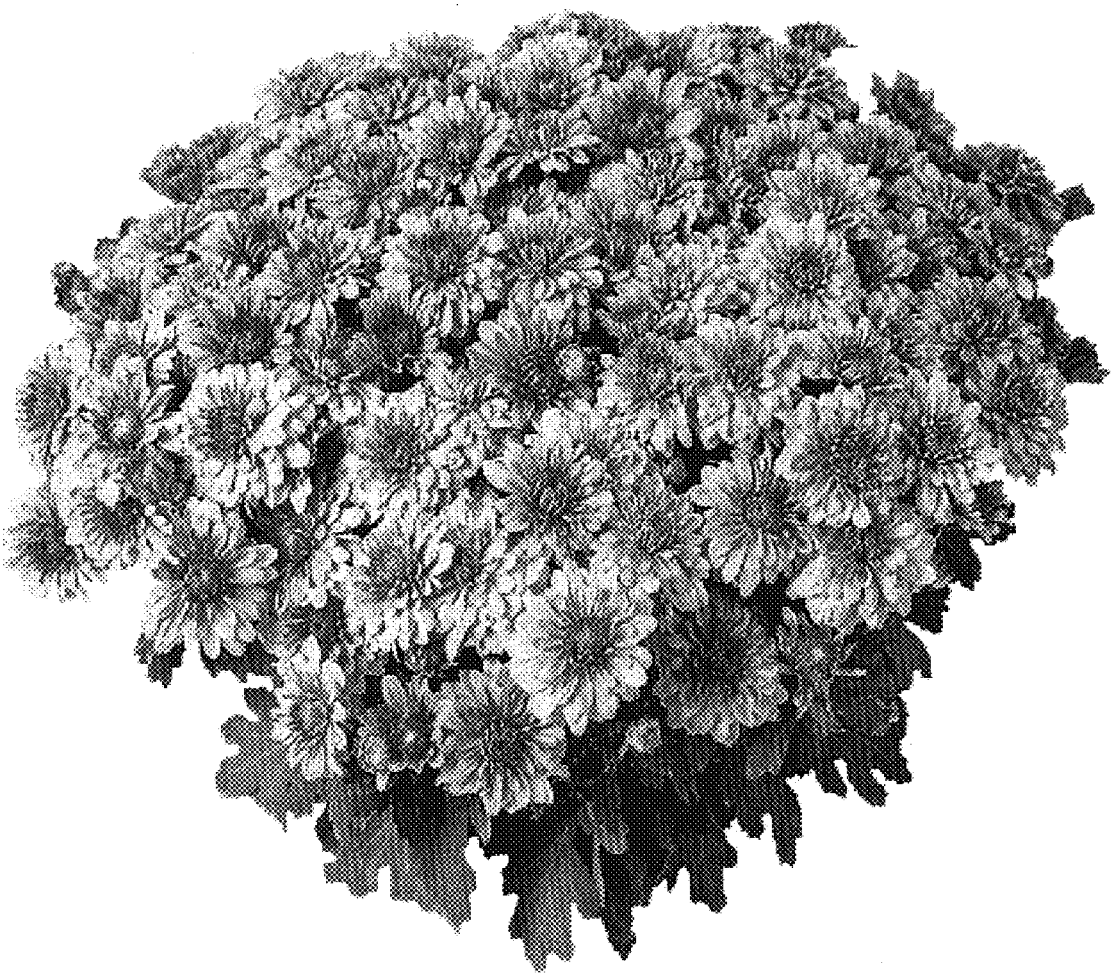

* * * * *